US010913978B2

United States Patent
Ivanov et al.

(10) Patent No.: US 10,913,978 B2
(45) Date of Patent: Feb. 9, 2021

(54) APPARATUS AND METHODS FOR CONTINUOUS DIAGNOSTICS OF MACROMOLECULES

(71) Applicant: AXBIO INC., Santa Clara, CA (US)

(72) Inventors: Igor Ivanov, Santa Clara, CA (US); Licheng Niu, Santa Clara, CA (US); Albert Chueh, Santa Clara, CA (US); Hui Tian, Santa Clara, CA (US); Suhua Deng, Santa Clara, CA (US)

(73) Assignee: AXBIO INC., Santa Clara, CA (US)

( * ) Notice: Subject to any disclaimer, the term of this patent is extended or adjusted under 35 U.S.C. 154(b) by 57 days.

(21) Appl. No.: 15/893,983

(22) Filed: Feb. 12, 2018

(65) Prior Publication Data

US 2018/0230531 A1  Aug. 16, 2018

Related U.S. Application Data

(60) Provisional application No. 62/458,840, filed on Feb. 14, 2017.

(51) Int. Cl.
| | | |
|---|---|---|
| *C12Q 1/6869* | (2018.01) | |
| *G01N 33/487* | (2006.01) | |
| *B01L 3/00* | (2006.01) | |
| *G01N 27/447* | (2006.01) | |

(52) U.S. Cl.
CPC ...... *C12Q 1/6869* (2013.01); *B01L 3/502707* (2013.01); *B01L 3/502715* (2013.01); *B01L 3/502738* (2013.01); *G01N 27/44791* (2013.01); *G01N 33/48721* (2013.01); *B01L 2300/0645* (2013.01); *B01L 2300/0861* (2013.01); *B01L 2300/0896* (2013.01); *B01L 2400/0622* (2013.01)

(58) Field of Classification Search
CPC ....... G01N 33/48721; C12Q 1/68; B81B 1/00
See application file for complete search history.

(56) References Cited

U.S. PATENT DOCUMENTS

| | | | |
|---|---|---|---|
| 4,445,538 A * | 5/1984 | Bilski | F16K 11/168 137/596.2 |
| 6,485,690 B1 | 11/2002 | Pfost et al. | |
| 8,380,541 B1 | 2/2013 | Holmes et al. | |
| 8,722,327 B2 | 5/2014 | Cao et al. | |
| 9,116,139 B2 | 8/2015 | Kain et al. | |
| 9,127,313 B2 * | 9/2015 | Brown | G01N 27/44756 |
| 9,428,793 B2 | 8/2016 | Chui et al. | |

(Continued)

FOREIGN PATENT DOCUMENTS

| | | |
|---|---|---|
| CN | 101675169 A | 3/2010 |
| CN | 103305402 | 9/2013 |

(Continued)

OTHER PUBLICATIONS

International Search Report and Written Opinion for Application No. PCT/US2018/017762, dated Jun. 7, 2018, 12 pages.

(Continued)

*Primary Examiner* — Louis J Rufo
*Assistant Examiner* — Caitlyn Mingyun Sun

(57) ABSTRACT

Devices, apparatus and methods for sequencing macromolecules are disclosed. The devices and apparatus include independently controllable fluid channels bi-directionally coupled to a measurement module.

24 Claims, 4 Drawing Sheets

(56) References Cited

U.S. PATENT DOCUMENTS

| | | | |
|---|---|---|---|
| 2006/0105461 A1* | 5/2006 | Tom-Moy | C12Q 1/6825 436/43 |
| 2009/0167288 A1 | 7/2009 | Reid et al. | |
| 2012/0024700 A1 | 2/2012 | Boccardi et al. | |
| 2012/0028845 A1 | 2/2012 | Teggatz et al. | |
| 2012/0037251 A1* | 2/2012 | Ohmer | F15B 11/006 137/637 |
| 2012/0267729 A1 | 10/2012 | Dang et al. | |
| 2013/0140192 A1* | 6/2013 | Behrends | G01N 33/48728 205/792 |
| 2013/0260472 A1 | 10/2013 | Holt | |
| 2013/0345065 A1 | 12/2013 | Hasibi et al. | |
| 2014/0110259 A1 | 4/2014 | Takahashi et al. | |
| 2015/0060277 A1* | 3/2015 | Golovchenko | B01L 3/502761 204/453 |
| 2015/0125872 A1 | 5/2015 | Chen et al. | |
| 2018/0223351 A1 | 8/2018 | Davis et al. | |

FOREIGN PATENT DOCUMENTS

| | | |
|---|---|---|
| CN | 103429997 | 12/2013 |
| CN | 104254771 A | 12/2014 |
| CN | 105637081 | 6/2016 |
| CN | 106164295 | 11/2016 |
| WO | 2016/154302 A1 | 9/2016 |

OTHER PUBLICATIONS

Hu, Ying et al., "Detection of Analysis of DNA Recapture Through a Solid-State Nanopore," Chinese Science Bulletin, Oct. 2014, vol. 59, No. 35, p. 4953-4959.

Non-Final Office Action for U.S. Appl. No. 15/628,517, dated Jul. 17, 2018, 10 pages.

Final Office Action for U.S. Appl. No. 15/628,517, dated Jan. 15, 2019, 12 pages.

Search Report for Application No. PCT/US2017/038376, dated Sep. 19, 2017, 10 pages.

International Search Report and Written Opinion for Application No. PCT/US2017/038376, dated Nov. 9, 2017, 16 pages.

International Preliminary Report on Patentability for Application No. PCT/US2017/038376, dated Jan. 3, 2019, 9 pages.

* cited by examiner

APPARATUS AND METHODS FOR CONTINUOUS DIAGNOSTICS OF MACROMOLECULES

This application claims the benefit under 35 U.S.C. § 119(e) of U.S. Provisional Application No. 62/458,840, filed on Feb. 14, 2017, which is incorporated by reference in its entirety.

FIELD

The present invention relates to devices, apparatus and methods for sequencing macromolecules. The devices and apparatus include independently controllable fluid channels bi-directionally coupled to a measurement module.

BACKGROUND

Both solid-state nanopores and biological nanopores are increasingly the focus of considerable effort in the development of a low cost, high throughput macromolecule sequencing systems. An approach in nanopore-based sensing employs the measurement of ionic current flow through a nanopore that is incorporated within a highly resistive amphiphilic membrane between electrodes provided on either side of the membrane. As a macromolecule such as a deoxyribonucleic acid (DNA) polynucleotide is caused to translocate through the nanopore, the ionic current flow through the nanopore is modulated by the different nucleotide bases of the DNA strand. Measurement in changes in ionic current flow can be carried out in order to determine a sequence characteristic of the polymer strand.

Despite significant advances, providing manufacturable large array integrated nanopore sensing devices is challenging. Variations in the device quality among modules can lead to poor signal to noise ratios and differences in the osmolality of the solutions on either side of the nanopore-containing membrane can cause reliability issues. Furthermore, methods for controlling the rate at which a macromolecule is translocated across the nanopore can be less than ideal, resulting in high error rates.

SUMMARY

Devices, apparatus and methods for sequencing macromolecules are disclosed. The devices and apparatus include independently controllable fluid channels bi-directionally coupled to measurement modules.

According to the present invention, macromolecule sequencing devices comprises measurement module comprising a first module inlet and a second module inlet; a first channel fluidly coupled to the first module inlet, wherein the first channel comprises a first channel inlet and a second channel inlet; a second channel fluidly coupled to the second module inlet, wherein the second channel comprises a third channel inlet and a fourth channel inlet; a first valve assembly configured to control bidirectional flow of a first solution in the first channel; and a second valve assembly configured to control bidirectional flow of a second solution in the second channel.

According to the present invention, methods of assembling a macromolecular sequencing module comprise providing the macromolecule sequencing device according to the present disclosure; flowing a first solution through the measurement module; flowing a first lipid-containing solution through the second channel; flowing a second solution through the second channel; and flowing a third solution through the second channel.

According to the present invention, methods of sequencing a macromolecule comprise providing the macromolecular sequencing device according to the present disclosure, wherein the sequencing device comprises a nanopore-containing bilayer membrane disposed within the measurement module and separating a first volume and a second volume; introducing a macromolecule into the second volume; causing the macromolecule to be translocated from the second volume into the first volume through the nanopore; and detecting a property correlated with the translocation of the macromolecule through the nanopore.

According to the present invention, macromolecule sequencing apparatus comprise a plurality of the macromolecule sequencing devices according to the present disclosure.

According to the present invention, methods of sequencing a macromolecule comprise forming a nanopore membrane in a first module wherein the nanopore membrane separates a first volume and a second volume; introducing a macromolecule into a first volume; reading a sequence of a single strand of the macromolecule as the macromolecule is translocated through the nanopore from the first volume into the second volume; collecting the single stranded macromolecule in an intermediate reservoir; forming a nanopore membrane in a second module wherein the nanopore membrane separates a first volume and a second volume; preparing the single stranded macromolecule for sequencing-by-synthesis; and performing SBS sequencing as the SBS-prepared single stranded macromolecule translocates from the first volume to the second volume of the second module.

BRIEF DESCRIPTION OF THE DRAWINGS

Those skilled in the art will understand that the drawings described herein are for illustration purposes only. The drawings are not intended to limit the scope of the present disclosure.

DETAILED DESCRIPTION

Figure 1:
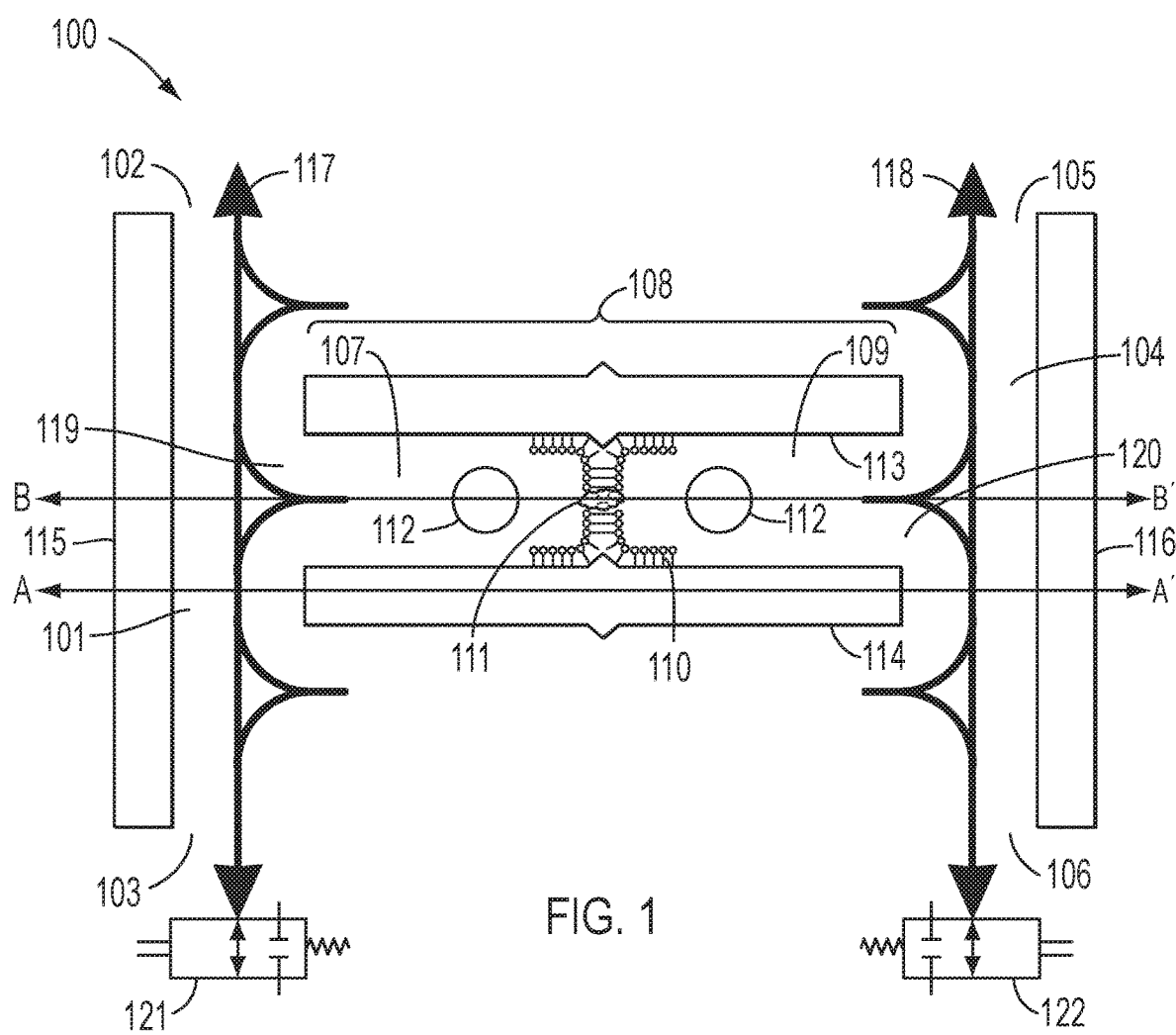
FIG. 1 shows a top cross-sectional view of a macromolecule sequencing module provided by the present disclosure.

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of about 1 and the recited maximum value of about 10, that is, having a minimum value equal to or greater than about 1 and a maximum value of equal to or less than about 10. Also, in this application, the use of "or" means "and/or" unless specifically stated otherwise, even though "and/or" may be explicitly used in certain instances.

Reference is now made to certain apparatus and methods of the present invention. The disclosed apparatus and methods are not intended to be limiting of the claims. To the contrary, the claims are intended to cover all alternatives, modifications, and equivalents.

"Nanopore" refers to a pore, channel or passage formed or otherwise provided in a membrane. A membrane may be an organic membrane, such as an amphiphilic bilayer or lipid bilayer, or a synthetic membrane, such as a membrane formed of a polymeric material. or a solid state membrane formed of metal, metal oxide, and/or an intermetallic. The nanopore may be disposed adjacent or in proximity to a sensing circuit or an electrode coupled to a sensing circuit, such as, for example, a complementary metal-oxide semiconductor (CMOS) or field effect transistor (FET) circuit. A nanopore can have a characteristic width or diameter on the order of 0.1 nanometers (nm) to about 1,000 nm. A nanopore can comprise a protein or protein complex such as, for example, α-hemolysin.

"Macromolecule" refers to a biological polymer such as, for example, a polynucleotide including DNA and RNA, or a protein. A macromolecule can comprise, for example, DNA, DNA fragments, RNA, RNA fragments, including mRNA (messenger ribonucleic acid) and rRNA (ribosomal ribonucleic acid) and fragments thereof, PNA, nucleotides, nucleosides, oligonucleotides, proteins, polypeptides, ammo acids, and polymers. The macromolecules can be single stranded.

"Polynucleotide" refers to a polymer or oligomer comprising one or more nucleotides. A polynucleotide may comprise a DNA polynucleotide or oligonucleotide, a RNA polynucleotide or oligonucleotide including mRNA and rRNA, or one or more sections of DNA polynucleotide or oligonucleotide and/or RNA polynucleotide or oligonucleotide.

A "nucleotide" can be a primary nucleotide or a nucleotide analog. A primary nucleotide can be deoxyadenosine mono-phosphate (dAMP), deoxycytidine mono-phosphate (dCMP), deoxyguanosine mono-phosphate (dGMP), deoxythymidine mono-phosphate (dTMP), adenosine mono-phosphate (AMP), cytidine mono-phosphate (CMP), guanosine mono-phosphate (GMP) or uridine mono-phosphate (UMP). A nucleotide analog is an analog or mimic of a primary nucleotide having modification on the primary nucleobase (A, C, G, T and U), the deoxyribose/ribose structure, the phosphate group of the primary nucleotide, or any combination thereof. For example, a nucleotide analog can have a modified base, either naturally existing or man-made. Examples of modified bases include methylated nucleobases, modified purine bases (e.g., hypoxanthine, xanthine, 7-methylguanine, isodG), modified pyrimidine bases (e.g., 5,6-dihydrouracil and 5-methylcytosine, isodC), universal bases (e.g., 3-nitropyrrole and 5-nitroindole), non-binding base mimics (e.g., 4-methylbezimidazole and 2,4-difluorotoluene or benzene), and no base (a basic nucleotide where the nucleotide analog does not have a base). Examples of nucleotide analogs having modified deoxyribose (e.g., dideoxynucleosides such as dideoxyguanosine, dideoxyadenosine, dideoxythymidine, and dideoxycytidine) and/or phosphate structure (together referred to as the backbone structure) includes glycol nucleotides, morpholinos, and locked nucleotides.

Apparatus for sequencing macromolecules such as polynucleotides can comprise independently controllable channels fluidly coupled to a nanopore module. The solutions within the independently controllable channels can be changed to facilitate formation of lipid bilayers, introduction of a nanopore complex within a lipid bilayer, and/or polynucleotide sequencing. The channels can be fluidly coupled such that a solution in one channel can be reintroduced into the other channel. For example, a sequenced macromolecule such as a polynucleotide can be re-introduced into the nanopore module or another sequencing module for additional sequencing using the same or different sequencing methods.

Apparatus provided by the present disclosure provide for independent control of the solutions in a macromolecule sequencing module. The ability to independently control the solutions on either side of a nanopore-containing lipid bilayer can improve the stability of the lipid bilayer during sequencing of a macromolecule and can facilitate sequencing. The ability to re-introduce a previously sequenced macromolecule into a sequencing module for one or more additional sequencing operations (multiple reads) on the same macromolecule can improve the accuracy, the reliability, the fidelity, and the completeness of the sequencing.

A macromolecule sequencing module can comprise a nanopore complex extending through a lipid bilayer. The lipid bilayer separates a first volume and a second volume of a measurement module. By convention a sequencing module comprises a first chamber, which can be referred as the cis chamber, and a second chamber, which can be referred to as the trans chamber, where the cis and trans chambers can be separated by a nanopore-containing bilayer membrane. A macromolecule being sequenced can be translocated through the nanopore from the cis chamber to the trans chamber. During sequencing, a solution comprising a macromolecule such as a polynucleotide can be introduced into a first volume. The polynucleotide is caused to translocate through the nanopore from a first volume into a second volume. As the polynucleotide passes through the nanopore, the electrochemical potential across the membrane can be measured and correlated with the nucleotide sequence passing through the nanopore at a given time. The accumulated electrochemical measurements and nucleotide sequence correlations can result in a determination of the polynucleotide sequence.

It is desirable that the solution on either side of the lipid bilayer be independently controllable. By independently controllable is meant that the solutions on either side of the lipid bilayer can have different compositions and different properties. Throughout the device assembly process in which, for example, the lipid bilayer is formed and the nanopore complex inserted into the lipid bilayer, it can be desirable to independently introduce and change solutions on either side of the nanopore module. During formation of the lipid bilayer, the solutions on either side of the lipid bilayer may be characterized, for example, by a different hydrophilicity/hydrophobicity. During sequencing, the solutions on either side of the lipid bilayer may be characterized by a different osmolality.

A microfluidic macromolecule sequencing device can comprise at least one macromolecule sequencing module fluidly coupled to a first channel and to a second channel on either side of the sequencing module. The channels can be coupled to one or more reservoirs. The microfluidic device including the walls defining the channels, modules, and reservoirs can be formed of any suitable materials such as organic and/or inorganic materials, including, for example, microelectronic materials, whether electrically conducting, electrically semiconducting, or electrically insulating, including materials such as II-IV and III-V materials, oxides and nitrides, such as $Si_3N_4$, $Al_2O_3$, and SiO, organic and inorganic polymers such as polyamide, plastics such as Teflon™ or elastomers such as silicone, and glasses. A solid state support structure may be formed from monoatomic layers, such as graphene, molybdenum disulfide, or boron nitride. Walls of a microfluidic device may be functionalized or treated with an inorganic or organic layer to provide certain properties to the side walls such as, for example, hydrophilicity, hydrophobicity, and/or hydrogen bonding capacity.

The diameter of a channel may be, for example, from 10 nm to about 1,000 nm, for example, from 10 nm to 100 nm, or from 10 nm to 50 nm. A channel can include openings or inlets at both ends, and a macromolecule dissolved or suspended in a solution may pass through the first channel from one inlet to the other inlet. A channel inlet can also serve as an outlet depending on the configuration of the fluid valve or fluid valves coupled to the channel inlets. For convenience, the term inlet is meant to refer to both an inlet for fluid flowing into a channel and an outlet for fluid flowing out of a channel. Whether an inlet functions as an inlet or as an outlet can be determined from the context of use. An inlet can function as either an inlet or as an outlet at different times during use of a sequencing apparatus. At a particular time a channel inlet can be used as an inlet for fluid flowing through a channel or can be used as an outlet for fluid flowing through the channel. A channel can comprise an inlet on either end of the channel, or can comprise a plurality of inlets. Some of the plurality of inlets may provide for unidirectional flow of solution through the channel and some of the plurality of inlets may provide for bidirectional flow through the channel. A macromolecule may be introduced into a first volume of a macromolecule sequencing module. The macromolecule within the first volume can pass through a nanopore disposed within a bilayer membrane and into a second volume of the macromolecule sequencing module. A macromolecule may be dissolved or suspended in any suitable solution as a solute in a solution. The solution may be, for example, an aqueous solution, organic solution, or a combination thereof. An aqueous solution may have a certain pH such as, for example, within a range from pH 2 to pH 12, from pH 2 to pH 7, or from pH 7 to pH 14.

The reservoirs or other components of the nanopore sensor may be configured to provide a driving force for moving a macromolecule toward and/or through a nanopore or through the nanopore from one of the reservoirs to another of the reservoirs. For example, electrodes can be provided in a circuit with voltage and current to produce an electrophoretic force between the reservoirs for electrophoretically driving the macromolecules in the solution, toward the nanopore or through the nanopore from one reservoir to another reservoir. To enable electrophoretic driving of the macromolecules, the solutions within the reservoirs can be provided as electrically conductive ionic solutions having pH and other characteristics that are suitable for the macromolecules in the solution. Translocation and control of the rate of translocation of macromolecules though a nanopore can also be carried out using alternative techniques, such as using an enzyme molecular motor.

In addition to or as an alternative to an applied voltage driving force, a pressure gradient across the pore can be used to bring molecules towards the nanopore and/or through the nanopore. A pressure gradient can be produced by using a physical pressure, or a chemical pressure such as an osmotic pressure. An osmotic pressure can be produced from a concentration difference across the cis and trans chambers. The osmotic pressure can be produced by having a concentration gradient of an osmotically active agent, such as, for example, a salt, polyethylene glycol (PEG), or glycerol. Also, optical tweezers or magneto-optic traps may be used to manipulate single nucleotides, parts of macromolecule, or whole macromolecules.

Lipid bilayers are thin polar membranes formed from two layers of lipid molecules. The amphipathic molecules for forming a lipid bilayer can be any suitable amphipathic molecule that is capable of forming a membrane at the interfaces between a polar solution and a non-polar solution. An amphipathic molecule may comprise a lipid, which may have a single component or a mixture of components, as is conventional when forming lipid bilayers. Any lipids capable of forming a lipid bilayer may be used. The lipids can be chosen such that a lipid bilayer having the required properties, such as surface charge, ability to support membrane proteins such as a nanopore, packing density or mechanical properties, is formed. The lipids can comprise one or more different lipids. For instance, the lipids can contain up to 100 lipids. The lipids preferably contain 1 to 10 lipids. The lipids may comprise naturally-occurring lipids and/or artificial lipids.

Lipids can comprise a head group, an interfacial moiety and two hydrophobic tail groups which may be the same or different. Suitable head groups include, for example, neutral head groups, such as diacylglycerides and ceramides; zwitterionic head groups, such as phosphatidylcholine, phosphatidylethanolamine and sphingomyelin; negatively charged head groups, such as phosphatidylglycerol; phosphatidylserine, phosphatidylinositol, phosphatic acid and cardiolipin; and positively charged headgroups, such as trimethylammonium-propane. Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-dodecanolic acid), myristic acid (n-tetradecononic acid), palmitic acid (n-hexadecanoic acid), stearic acid (n-octadecanoic) and arachidic (n-eicosanoic); unsaturated hydrocarbon chains, such as oleic acid (cis-9-octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester.

Lipids can also be chemically-modified. The head group or the tail group of the lipids may be chemically-modified. Suitable lipids in which a head group has been chemically-modified include, for example, PEG-modified lipids, such as 1,2-diacyl-sn-glycero-3-phosphoethanolamine-N-[methoxy(polyethylene glycol)-2000]; functionalized PEG lipids, such as 1,2-distearoyl-sn-glycero-3 phosphoethanolamine-N-[biotinyl(polyethylene glycol)2000]; and lipids modified for conjugation, such as 1,2-dioleoyl-sn-glycero-3-phosphoethanolamine-N-(succinyl) and 1,2-dipalmitoyl-sn-glycero-3-phosphoethanolamine-N-(biotinyl). Suitable lipids whose tail groups have been chemically-modified include, for example, polymerizable lipids, such as 1,2-bis(10,12-tricosadiynoyl)-sn-glycero-3-phosphocholine; fluorinated lipids, such as 1-palmitoyl-2-(16-fluoropalmitoyl)-sn-glycero-3-phosphocholine; deuterated lipids, such as 1,2-dipalmitoyl-$D_{62}$-sn-glycero-3-phosphocholine; and ether linked lipids, such as 1,2-di-O-phytanyl-sn-Glycero-3-phosphocholine. Examples of suitable lipids include phytanoyl lipids such as 1,2-diphytanoyl-sn-glycero-3-phosphocholine (DPhPC) and 1,2-diphytanoyl-sn-glycero-3-phosphoethanolamine (DPhPE). Amphipathic polymer membranes can be used.

An amphipathic molecule may comprise an amphipathic compound comprising a first outer hydrophilic group, a hydrophobic core group, and a second outer hydrophilic group, wherein each of the first and second outer hydrophilic groups is linked to the hydrophobic core group.

An amphipathic molecule can comprise a triblock copolymer. Triblock copolymers can withstand high voltages, their robustness as well as their ability to withstand biological degradation from detergents and proteins. Examples of suitable silicone triblock polymers that may be employed are 7-22-7 PMOXA-PDMS-PMOXA, 6-45-6 PMOXA-PE-PMOXA, and 6-30-6 PMOXA-PDMS-PMOXA. In order to stabilize lipid bilayer, certain functional groups may be inserted into lipid chain to allow cross-linking of individual lipids within the bilayer after formation and insertion of a nanopore. Cross-linking may be done any suitable method such as using thermal, UV, or metal ion-catalyzed methods.

A nanopore may be provided as an aperture, gap, channel, groove, pore or other hole in a lipid bilayer and is provided with an extent, such as a diameter, for a corresponding geometry, that is suitable for translocating and sensing macromolecules. For sensing molecule translocation through the nanopore, a nanopore can be characterized by a diameter, for example, less than 10 nm, less than 5 nm, less than 2 nm, or less than 1 nm.

A nanopore may be a transmembrane protein pore. A biological pore may be a naturally occurring pore or may be a mutant pore. Examples of suitable nanopores are described, for example, in U.S. Application Publication No. 2012/1007802; Stoddart et al., *Proc Natl Acad Sci*, 12; 106(19):7702-7, Stoddart et al., *Angew Chem Int Ed Engl.* 2010; 49(3):556-9, Stoddart et al., *Nano Lett.* 2010 Sep. 8; 10(9):3633-7, Butler et al., *Proc Natl Acad Sci* 2008; 105 (52); 20647-52, U.S. Application Publication 2014/186823, and PCT International Application Publication No. WO 2013/153359. A nanopore may be homo-oligomeric or may be hetero-oligomeric. A nanopore may be a RNA or DNA origami pore, such as described by Langecker et al., *Science*, 2012; 338: 932-936.

Various methods can be used to detect and quantify the translocation of a macromolecule through a nanopore. For example, electrodes can be disposed within the cis and trans chambers, respectively. Electrodes can also be disposed within the bilayer membrane or on and/or within a wall of the measurement module.

An electrode can be sensitive to an electrical property, such as, for example, current, voltage, resistance, impedance, electrical potential, or a combination of any of the foregoing.

Optical detectors may also be used to sense and quantify the translocation of a macromolecule through the nanopore. An optical detector may be sensitive to, for example, absorbance, transmission, scattering, fluorescence, fluorescence resonance energy transfer (FRET), surface plasmon resonance, surface enhanced Raman scattering, tip enhanced Raman scattering, diffraction, and a combination thereof.

The detector may be sensitive to a probe bonded or attached to the macromolecule.

The nanopore sensor is not limited to solid state nanopore configurations with solid state voltage sensing devices. Biological nanopores and potential sensing arrangements can also be employed, e.g., with a protein nanopore or other suitable configuration. A voltage-sensitive dye, e.g., a fluorescent direct dye, can be provided in the lipid bilayer as an electrical transduction element. With this arrangement, when a species object such as a molecule translocates through the protein nanopore, the voltage drop across the amphiphilic layer changes and the fluorescence of the dye is modulated by the voltage change. Optical detection or sensing of the dye fluorescence and changes to that fluorescence provide sensing of the electrical potential at the nanopore. Optical microscopy or other conventional arrangement can be employed for making this potential measurement as an optical output signal from the nanopore sensor. This amphiphilic layer nanopore sensor is an example of a biological nanopore sensor that is based on sensing of the local potential at a site in the nanopore system. The method of local potential measurement for nanopore translocation detection is not limited to a particular solid state or biological configuration and can be applied to any suitable nanopore configuration.

By maintaining the osmolality of the solutions in the cis and trans chambers such that the difference in the osmolality of the two solutions is reduced or minimized, the integrity of the bilayer is improved. This allows the bilayer and the nanopore module to have a larger dimension. With larger dimension cis and trans chambers, the sensing electrodes can have a larger dimension. Because the electrodes are consumed during use, geometrically larger electrodes can lead to longer electrode life, which in turn can extend the operating life of the sequencing device.

Larger chamber volumes can also facilitate the use of multiple electrodes within the cis and/or trans chambers, which can increase the signal-to-noise ratio.

Methods provided by the present disclosure can be extended to provide multiple bilayer/nanopore stacks. For example, after a first nanopore-containing bilayer is formed, the process used to assemble the first nanopore-containing bilayer can be repeated to form one or more additional nanopore-containing bilayers.

The schematic views of nanopore sensor configurations provided herein that enable a local electrical potential sensing method for nanopore sensing. For clarity of discussion, device features illustrated in the figures are not shown to scale.

A top cross-sectional view of a sequencing module is shown in FIG. 1.

The sequencing module 100 shown in FIG. 1 includes a first channel 101, having a first inlet 102 and a second inlet 103 at opposite ends of the first channel 101; and a second channel 104 having a first inlet 105 and a second inlet 106 at opposite ends of the second channel 104. The inlets 102/103/105/106 are fluidly coupled to one or more valves 121/122 that are configured to independently control the flow of solutions through the first channel and through the second channel. The valves 121/122 can be configured to provide for bidirectional flow 117 through the first channel and for bidirectional flow 118 through the second channel. The valves 121/122 can also be configured to hold a solution in the channel without flowing the solution through the channel. The solution within a channel can exchange with the fluid within the first volume 107 and the second volume 109 of the measurement module 108.

Each of the one or more valves (not shown) can be fluidly coupled to one or more fluid reservoirs (not shown). The one or more fluid reservoirs can contain different solutions suitable for use in assembling the sequencing module 100 and/or for sequencing a macromolecule such as a polynucleotide. Examples of suitable fluids include buffers, solvents, alcoholic solvents, solutions containing lipids, solutions containing nanopore complexes, solutions containing macromolecules such as polynucleotides. The one or more reservoirs can be fluidly coupled to channels 102 and 104.

The first channel 101 can be fluidly coupled to a first volume 107 of a measurement module 108. Measurement module 108 includes a first module inlet 119, a first volume 107, a second module inlet 120, and a second volume 109. A lipid bilayer 110 can be disposed at in interface between the first volume 107 and the second volume 109. Lipid bilayer 110 can include a nanopore complex 111 disposed within the lipid bilayer 110 and fluidly coupling the first volume 107 and the second volume 109 of measurement module 108.

As shown in FIG. 1, electrodes 112 can be disposed within the first volume 107 and within the second volume 109. Electrodes 112 can be configured to measure a change in electrical potential between the first volume 107 and the second volume 109.

First channel 101, second channel 104, and measurement chamber 108 can be defined by sidewalls 113/114/115/116. Sidewalls 113/114/115/116 can comprise a suitable material used to fabricate microfluidic devices.

First and second channels 101/104 can have any suitable dimension such as, for example, less than 100 nm, less than 50 nm, or less than 20 nm.

Measurement module 108 can have any suitable dimension, such as the width of the measurement module between walls 113 and 114 can be less than 60 nm, less than 40 nm, or less than 20 nm.

Channels 101/104 can be fluidly coupled to one or more measurement modules. Channel 101 can be fluidly coupled to channel 104. Because channels 101 and 104 are fluidly coupled, a macromolecule that has been translocated from the second volume 109 to the first volume 107 through nanopore complex 111 can enter first channel 101, be directed to second channel 104, and be reintroduced into the second volume 109, where the introduced macromolecule can again be sequenced. The re-introduced macromolecule can be introduced into the same measurement module or into a different measurement module.

Figure 2:
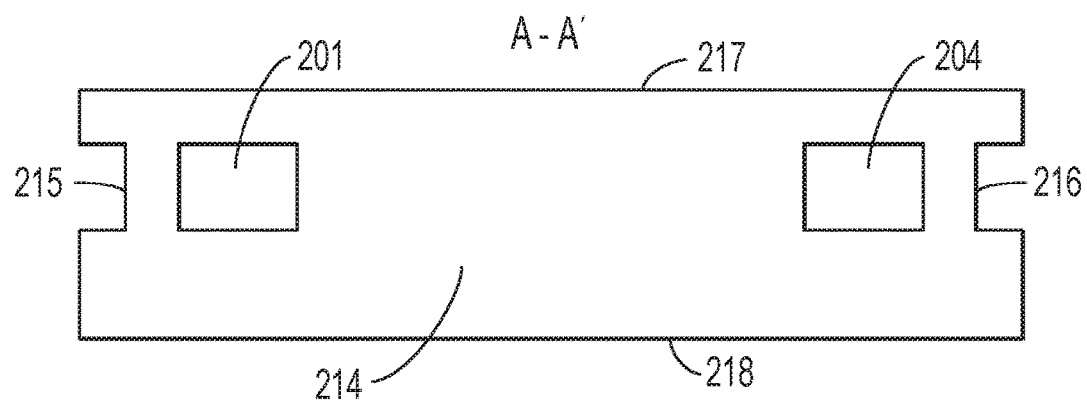
FIG. 2 shows a vertical cross-sectional side view along section A-A' of the macromolecule sequencing module shown in FIG. 1.

FIG. 2 shows a cross-sectional view along section A-A' of the sequencing module shown in FIG. 1. FIG. 2 shows the first channel 201, the second channel 204, and sidewalls 214/215/216. FIG. 2 also shows a top plate 217 and a bottom plate 218, which together with sidewalls 113/114/115/116 define a sequencing module.

Figure 3:
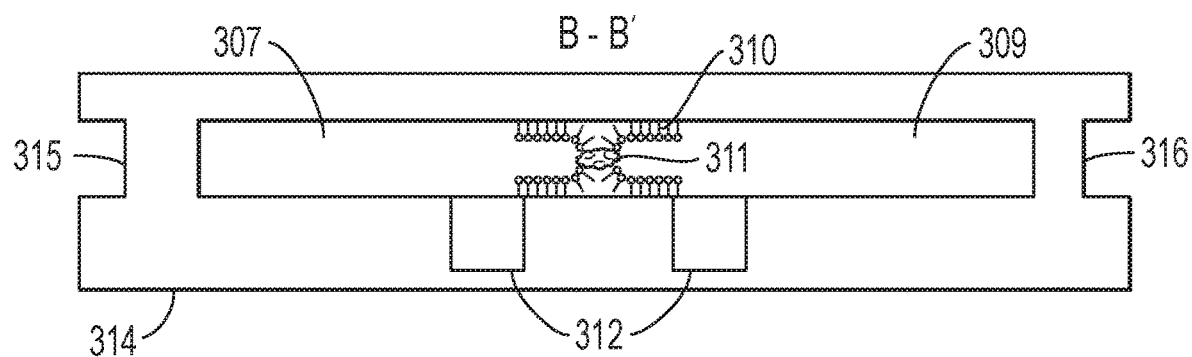
FIG. 3 shows a vertical cross-sectional side view along section B-B' of the macromolecule sequencing module shown in FIG. 1.

FIG. 3 shows a cross-sectional view along section B-B' of the sequencing module shown in FIG. 1. FIG. 3 shows sidewalls 314/315/316, first volume 309 and the second volume 307, nanopore complex 311 disposed within lipid bilayer 310, and electrodes 312.

A sequencing device can comprise a plurality of sequencing modules.

The plurality of sequencing modules can be arranged in a two-dimensional array, a three-dimensional array, or in any suitable configuration. In can be desirable to include multiple sequencing modules in a small area to enhance sequencing efficiency. A sequencing apparatus can comprise, for example, up to $10^5$ sequencing modules, up to $10^6$ sequencing modules, or 10' sequencing modules.

Figure 4:
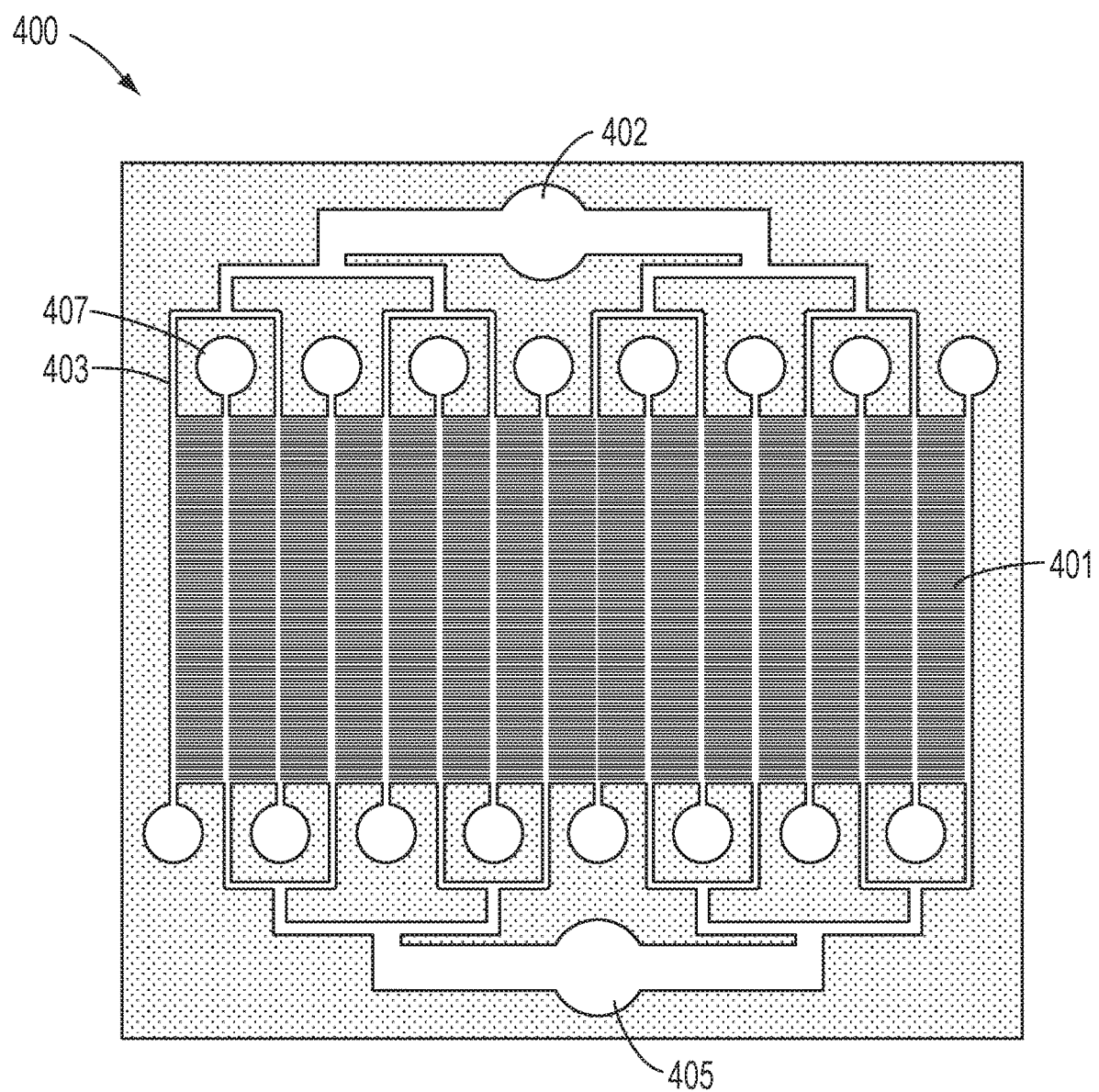
FIG. 4 shows a top view of a macromolecule sequencing apparatus comprising a plurality of macromolecule sequencing modules.

For example, top cross-sectional view of a sequencing device 400 comprising a plurality of sequencing modules 401 is shown in FIG. 4. FIG. 4 shows a plurality of sequencing modules 401 arranged in parallel arrays.

A first side of each measurement modules of each of the plurality of sequencing modules 401 is fluidly coupled to a first fluid reservoir 402 by channels 403. Each channel 403 is also fluidly coupled to a second fluid reservoir 404.

A second side of each measurement chamber of each of the plurality of sequencing modules is fluidly coupled to a third fluid reservoir 405 by channels 406. Each channel 406 is also fluidly coupled to a fourth fluid reservoir 407.

Other configurations are included within the scope of the disclosure. For example, each channel may be fluidly coupled to a plurality of reservoirs. Each of the reservoirs may be fluidly coupled to one or more valves configured to control the flow of solution within the reservoirs to one or more measurement modules. The valves or valve assemblies can be configured to control the bidirectional flow of solution through the channels.

The sequencing device is only an example and other configurations are included. For example, each measurement chamber can be fluidly coupled to a plurality of fluid reservoirs and the different fluid reservoirs can be fluidly coupled to each other.

A nanopore lipid bilayer can be formed, for example using the following procedure.

Referring to FIG. 1 a suitable buffer can be allowed to flow from inlets 102 and 103, into channel 102, through measurement module 108, into channel 104, and out of channel 104 through inlets 105 and 106. The flow of buffer can be used to clean, restore, or otherwise prepare the device for use. The flow of buffer can remove air from the system including from the channels and measurement module. The buffer can comprise a wetting agent such as an alcohol to facilitate removal of air from the system. Additionally, bubbles can be removed by evacuating dissolved gases from solution using controlled vacuum conditions. Flowing a solution through a channel includes introducing a solution into a channel sufficient to displace a previous fluid within the channel, continuously flowing a solution through a channel from a first inlet through a second inlet of the channel, and introducing a solution into a channel sufficient to displace a previous fluid and maintaining the solution within the channel to allow for the exchange or mixing of the solution within the channel with the solution within the measurement module. Flowing a solution through or within a channel includes continuous flow and dis-continuous flow.

After the device is cleaned and air removed from the system, a lipid bilayer can be assembled within a measurement module. Assembly of the lipid bilayer can be accomplished by allowing a solution containing a lipid to flow from inlet 105, through channel 104, and out inlet 106. During this step of introducing lipids into the measurement module, inlets 102 and 103 of the first channel can be closed. The lipid solution flows into a portion of the measurement module. Referring to FIG. 1, a lipid monolayer will spontaneously form at the interface between the buffer and the lipid solution on the right side of the measurement module.

Still with inlets 102 and 103 blocked, a buffer solution can be introduced through inlet 105, into channel 104, and through inlet 106. During this process a layer of the second buffer solution will be present on the right side of the lipid monolayer and form a second solvent/buffer interface.

The lipid will spontaneously form a lipid monolayer at the interface between the solvent adjacent the first lipid monolayer and the second lipid-containing solution. The resulting structure, from left to right, includes a hydrophilic buffer, a lipid monolayer, a hydrophobic solution, a lipid monolayer and a hydrophilic buffer. The lipid monolayers then coalesce and displace the interfacial hydrophobic solution to form a bilayer membrane. A lipid bilayer membrane spans the width of the measurement module and defines a first volume and a second volume on either side of the lipid bilayer.

An alcoholic solution can be flushed through the inlets and both channels to remove any residual hydrophobic solution from the device.

To introduce a nanopore complex into the bilayer membrane, the osmotic conditions of the left and right sides of the measurement module, volumes 107 and 109 in FIG. 1, can be controlled by flowing suitable solutions from inlet 104, through channel 102, and through inlet 103; and from inlet 105 through channel 104, and through inlet 106. The solution flowing through inlet 103 and into channel 105 can comprise a nanopore complex. Upon introduction of the nanopore complex into the measurement module, the nanopore complex will spontaneously intercalate into the bilayer membrane.

After the nanopore complex is incorporated into the bilayer membrane, a polynucleotide can be sequenced. For example, a solution containing a single stranded polynucleotide can be introduced from p inlet 105 into channel 104 and into volume 109 of measurement module 108.

The dimensions of measurement chamber including the length, width and height can be selected to determine the rate at which a polynucleotide diffuses through the nanopore complex. For example, the dimensions of the chamber can determine the shape of the polynucleotide, which can affect the rate of polynucleotide diffusion through the nanopore complex. The walls of the measurement chamber can be coated with a layer of molecules to affect the shape and mobility of a polynucleotide.

Apparatus provided by the present disclosure provide for the independent control of the solutions on both sides of macromolecule sequencing module. The ability to independently control the solutions on the cis and trans sides of the macromolecule sequencing module can improve the reliability of the nanopore bilayer membrane system by reducing osmotic imbalance across the nanopore-containing bilayer membrane. Another advantage is that sequenced macromolecules in the trans chamber can be sequestered and recirculated to the cis chamber and re-sequenced. The ability to re-sequence a macromolecule can improve the sequencing reliability. By reducing the osmotic imbalance across the nanopore-containing bilayer membrane, the translocation rate can be controlled such that the rate is dominated by one-dimensional space restriction of Brownian motion of the macromolecule. Slowing the translocation of a macromolecule through the nanopore complex can improve the reliability and accuracy of the sequence determination.

Figure 5:
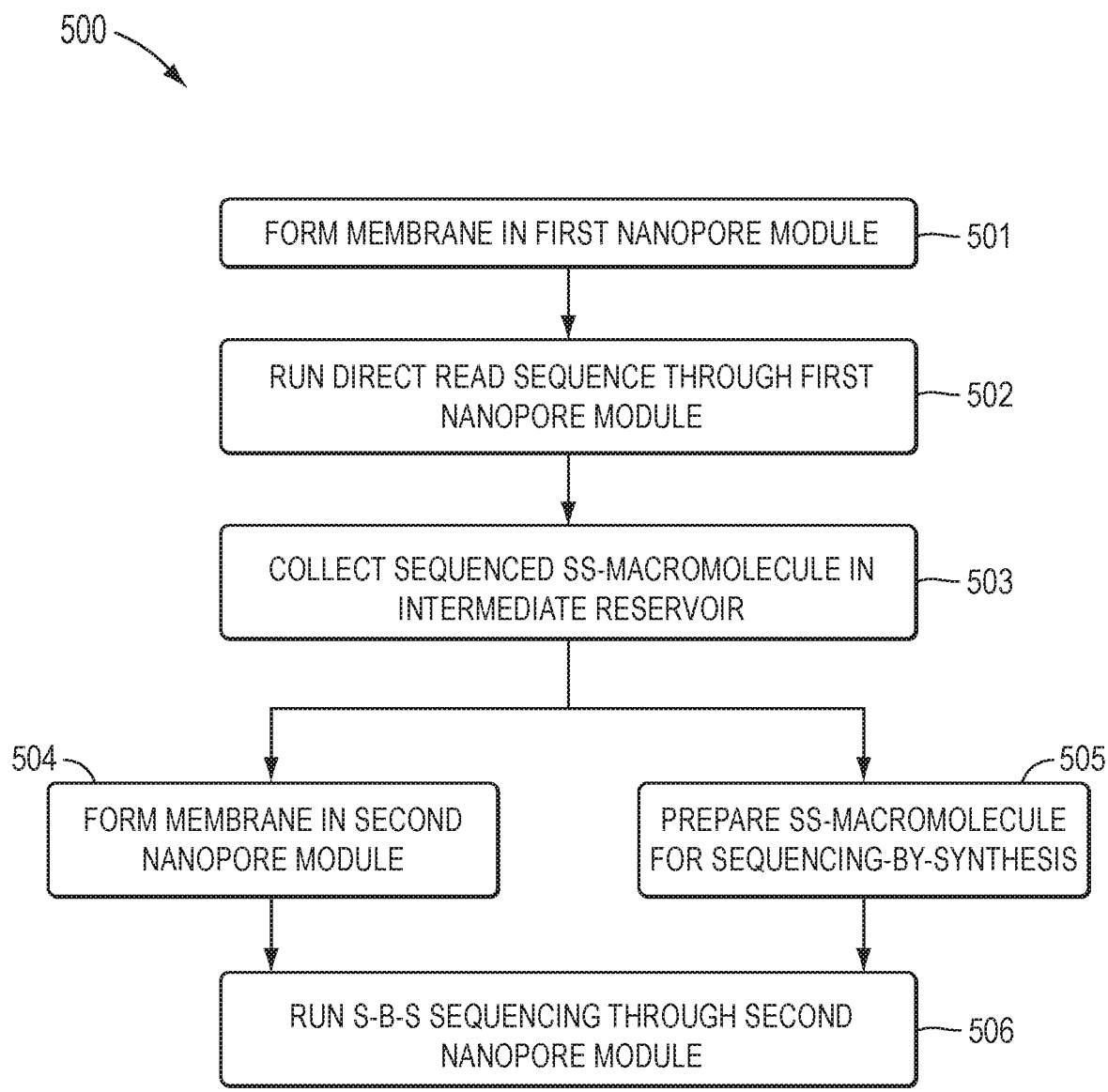
FIG. 5 shows a flow diagram illustrating certain methods for sequencing macromolecules according to the present disclosure.

Apparatus provided by the present disclosure can be used for sequencing macromolecules. FIG. 5 is a flow diagram illustrating certain methods for sequencing macromolecules according to the present disclosure. A first measurement module can be prepared by forming a nanopore membrane in the first measurement modules 501. A macromolecule is introduced into a cis chamber of a first module and the sequence is read as the single stranded macromolecule translocates through the nanopore into the trans chamber of the measurement module 502. The translocated single-stranded macromolecule is stored in an intermediate reservoir 503. A nanopore membrane can be formed in a second measurement module 504. The single stranded macromolecule from step 503 can be prepared for sequencing-by-synthesis ((SBS) 505. SBS sequencing on the SBS-prepared single stranded macromolecule is then performed in the second module 506.

Aspects of Invention

Aspect 1. A macromolecule sequencing device comprising: a measurement module comprising a first module inlet and a second module inlet; a first channel fluidly coupled to the first module inlet, wherein the first channel comprises a first channel inlet and a second channel inlet; a second channel fluidly coupled to the second module inlet, wherein the second channel comprises a third channel inlet and a fourth channel inlet; a first valve assembly configured to control bidirectional flow of a first solution in the first channel; and a second valve assembly configured to control bidirectional flow of a second solution in the second channel.

Aspect 2. The macromolecule sequencing device of aspect 1, comprising a nanopore-containing bilayer membrane disposed within the measurement module and separating a first volume and a second volume, wherein the first channel is fluidly coupled to the first volume and the second channel is fluidly coupled to the second volume.

Aspect 3. The macromolecule sequencing device of aspect 2, further comprising: a first electrode operatively coupled to the first volume; and a second electrode operatively coupled to the second volume.

Aspect 4. The macromolecule sequencing device of any one of aspects 1 to 3, comprising a plurality of measurement modules, wherein, the first inlet of each of the plurality of measurement modules is fluidly coupled to the first channel; and the second inlet of each of the plurality of measurement modules is fluidly coupled to the second channel.

Aspect 5. The macromolecule sequencing device of any one of aspects 1 to 4, wherein, the first solution is characterized by a first composition; the second solution is characterized by a second composition; and the first composition is different than the second composition.

Aspect 6. The macromolecule sequencing device of any one of aspects 1 to 5, wherein, the first solution is characterized by a first osmolality; the second solution is characterized by a second osmolality; and the first solution and the second solution are selected to control the difference between the first osmolality and the second osmolality.

Aspect 7. The macromolecule sequencing device of any one of aspects 1 to 6, wherein, the first solution is characterized by a first osmolality; the second solution is characterized by a second osmolality; and the first osmolality is substantially the same as the second osmolality.

Aspect 8. The macromolecule sequencing device of any one of aspects 1 to 7, wherein walls of the measurement module comprise a self-assembled monolayer.

Aspect 9. The macromolecule sequencing device of aspect 8, wherein the self-assembled monolayer is selected to stretch a macromolecule and to control mobility of a macromolecule.

Aspect 10. The macromolecule sequencing device of aspect 9, wherein the self-assembled monolayer is capable of forming hydrogen bonds to polynucleotides.

Aspect 11. The macromolecule sequencing device of aspect 9, wherein the self-assembled monolayer comprises a siloxane.

Aspect 12. The macromolecule sequencing device of any one of aspects 1 to 11, wherein the first channel is controllably, fluidly coupled to the second channel.

Aspect 13. A method of assembling a macromolecular sequencing module, comprising: providing the macromolecule sequencing device of any one of aspects 1 to 12; flowing a first solution through the measurement module; flowing a first lipid-containing solution through the second channel; flowing a second solution through the second channel; and flowing a third solution through the second channel.

Aspect 14. The method of aspect 13, wherein flowing a first solution through the measurement module comprises flowing a first solution from the first channel inlet and from the second channel inlet of the first channel through the third inlet and the fourth inlet of the second channel.

Aspect 15. The method of any one of aspects 13 to 14, wherein flowing a first lipid-containing solution through the second channel comprises flowing the first lipid-containing solution from the third inlet of the second channel through the fourth inlet of the second channel, wherein the first inlet and the second inlet of the first channel are closed.

Aspect 16. The method of any one of aspects 13 to 15, wherein flowing a second solution through the second channel comprises flowing the second solution from the third inlet of the second channel through the fourth inlet of the second channel, wherein the first inlet and the second inlet of the first channel are closed.

Aspect 17. The method of any one of aspects 13 to 16, wherein flowing a third solution through the second channel comprises flowing a third solution from the third inlet of the second channel through the fourth inlet of the second channel.

Aspect 18. The method of any one of aspects 13 to 17, wherein flowing the first solution comprises a wetting solvent.

Aspect 19. The method of any one of aspects 13 to 18, wherein flowing the third solution causes a lipid-solvent-lipid structure to form within the measurement module.

Aspect 20. The method of aspect 19, wherein, after flowing the third solution, the lipid-solvent-lipid structure coalesces to form a lipid bilayer within the measurement module.

Aspect 21. The method of aspect 20, further comprising, after a lipid bilayer is formed, flowing a fourth solution through the first channel and through the second channel, wherein the fourth solution comprises an alcoholic solvent.

Aspect 22. The method of aspect 20, further comprising, after a lipid bilayer is formed, introducing a nanopore complex into the lipid bilayer.

Aspect 23. The method of aspect 22, wherein introducing a nanopore complex comprises flowing a fifth solution through the second channel, wherein the fifth solution comprises a nanopore complex.

Aspect 24. The method of aspect 22, wherein introducing a nanopore complex further comprises simultaneously flowing a sixth solution through the first channel, wherein the sixth solution is selected to establish a desired osmolality condition.

Aspect 25. The method of any one of aspects 13 to 24, wherein each of the first solution, the second solution, and the third solution are hydrophilic.

Aspect 26. The method of claim 13, wherein the first lipid solution is hydrophobic.

Aspect 27. A method of sequencing a macromolecule, comprising: providing the macromolecular sequencing device of any one of aspects 1 to 12, wherein the sequencing device comprises a nanopore-containing bilayer membrane disposed within the measurement module and separating a first volume and a second volume; introducing a macromolecule into the second volume; causing the macromolecule to be translocated from the second volume into the first volume through the nanopore; and detecting a property correlated with the translocation of the macromolecule through the nanopore.

Aspect 28. The method of aspect 27, wherein, the first volume comprises a solution characterized by a first osmolality; the second volume comprises a second solution characterized by a second osmolality; and further comprising controlling the difference between the first osmolality and the second osmolality.

Aspect 29. The method of aspect 28, wherein controlling the difference between the first osmolality and the second osmolality comprises minimizing the difference between the first osmolality and the second osmolality.

Aspect 30. The method of aspect 28, wherein controlling the difference between the first osmolality and the second osmolality comprises introducing a solution characterized by a selected osmolality into the first volume.

Aspect 31. The method of aspect 28, wherein controlling the difference between the first osmolality and the second osmolality comprises introducing a solution into the first volume to establish a desired difference in osmolality between the solution in the first volume and the solution in the second volume.

Aspect 32. The method of any one of aspects 27 to 31, further comprising re-introducing the translocated macromolecule from the first volume into the second volume.

Aspect 33. The method of aspect 32, further comprising: causing the re-introduced macromolecule to be translocated from the second volume into the first volume through the nanopore; and detecting a property correlated with the translocation of the re-introduced macromolecule through the nanopore.

Aspect 34. A macromolecule sequencing apparatus comprising a plurality of the macromolecule sequencing devices of any one of aspects 1 to 12.

Aspect 35. The macromolecular sequencing apparatus of aspect 34, wherein at least some of the plurality of macromolecule sequencing devices comprise a nanopore-containing bilayer membrane disposed within the measurement module.

Aspect 36. The macromolecular sequencing apparatus of any one of aspects 34 to 35, wherein at least some of the plurality of macromolecule sequencing devices comprise a common first channel, a common second channel, or both a common first channel and a common second channel.

Aspect 37. The macromolecular sequencing apparatus of any one of aspects 34 to 36, wherein the common first channel is controllably, fluidly coupled to the common second channel.

Aspect 38. A method of sequencing a macromolecule comprising: forming a nanopore membrane in a first module wherein the nanopore membrane separates a first volume and a second volume; introducing a macromolecule into a first volume; reading a sequence of a single strand of the macromolecule as the macromolecule is translocated through the nanopore from the first volume into the second volume; collecting the single stranded macromolecule in an intermediate reservoir; forming a nanopore membrane in a second module wherein the nanopore membrane separates a first volume and a second volume; preparing the single stranded macromolecule for sequencing-by-synthesis; and performing SBS sequencing as the SBS-prepared single stranded macromolecule translocates from the first volume to the second volume of the second module.

It should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A macromolecule sequencing device comprising:
   a measurement module, wherein the measurement module comprises a first volume and a second volume;
   a first module inlet fluidly coupled to the first volume;
   a second module inlet fluidly coupled to the second volume;
   a first channel fluidly coupled to the first module inlet, wherein the first channel comprises a first channel inlet and a second channel inlet;
   a second channel fluidly coupled to the second module inlet, wherein the second channel comprises a third channel inlet and a fourth channel inlet;
   a nanopore-containing bilayer membrane disposed within the measurement module and separating the first volume and the second volume, wherein the first channel is fluidly coupled to the first volume and the second channel is fluidly coupled to the second volume;
   a first valve configured to control bidirectional flow of a first solution in the first channel; and
   a second valve configured to control bidirectional flow of a second solution in the second channel,
   wherein the first channel and the second channel are configured to reintroduce a sequenced macromolecule in the second volume entering the first channel and being directed to second channel back into the first volume of the measurement module or into a first volume of another measurement module.

2. The macromolecule sequencing device of claim 1, further comprising: a first electrode operatively coupled to the first volume; and a second electrode operatively coupled to the second volume.

3. The macromolecule sequencing device of claim 1, comprising a plurality of the measurement modules, wherein,
   the first inlet of each of the plurality of measurement modules is fluidly coupled to the first channel; and
   the second inlet of each of the plurality of measurement module is fluidly coupled to the second channel.

4. The macromolecule sequencing device of claim 1, wherein walls of the measurement module comprise a self-assembled monolayer.

5. The macromolecule sequencing device of claim 1, wherein the first channel is controllably, fluidly coupled to the second channel.

6. A method of assembling a macromolecular sequencing module, comprising:
   providing the macromolecule sequencing device of claim 1;
   flowing a first solution through the measurement module;
   flowing a first lipid-containing solution through the second channel;
   flowing a second solution through the second channel; and
   flowing a third solution through the second channel.

7. The method of claim 6, wherein flowing a first solution through the measurement module comprises flowing a first solution from the first channel inlet and from the second channel inlet of the first channel through the third inlet and the fourth inlet of the second channel.

8. The method of claim 6, wherein flowing the first lipid-containing solution through the second channel comprises flowing the first lipid-containing solution from the third inlet of the second channel through the fourth inlet of the second channel, wherein the first inlet and the second inlet of the first channel are closed.

9. The method of claim 6, wherein flowing a second solution through the second channel comprises flowing the second solution from the third inlet of the second channel through the fourth inlet of the second channel, wherein the first inlet and the second inlet of the first channel are closed.

10. The method of claim 6, wherein flowing a third solution through the second channel comprises flowing a third solution from the third inlet of the second channel through the fourth inlet of the second channel.

11. The method of claim 6, wherein flowing the first solution comprises a wetting solvent.

12. The method of claim 6, wherein flowing the third solution causes a lipid-solvent-lipid structure to form within the measurement module.

13. The method of claim 12, wherein, after flowing the third solution, the lipid-solvent-lipid structure coalesces to form a lipid bilayer within the measurement module.

14. The method of claim 13, further comprising, after the lipid bilayer is formed, flowing a fourth solution through the first channel and through the second channel, wherein the fourth solution comprises an alcoholic solvent.

15. The method of claim 13, further comprising, after the lipid bilayer is formed, introducing a nanopore complex into the lipid bilayer.

16. The method of claim 15, wherein introducing the nanopore complex comprises flowing a fifth solution through the second channel, wherein the fifth solution comprises the nanopore complex.

17. The method of claim 15, wherein introducing the nanopore complex further comprises simultaneously flowing a sixth solution through the first channel, wherein the sixth solution is selected to establish a desired osmolality condition.

18. The method of claim 6, wherein each of the first solution, the second solution, and the third solution are hydrophilic.

19. The method of claim 6, wherein the first lipid-containing solution is hydrophobic.

20. A method of sequencing a macromolecule, comprising:
   providing the macromolecular sequencing device of claim 1,
   introducing the macromolecule into the first volume;
   causing the macromolecule to be translocated from the first volume into the second volume through the nanopore; and detecting a property correlated with the translocation of the macromolecule through the nanopore to provide a sequenced macromolecule; and reintroducing the sequenced macromolecule in the second volume entering the second channel and being directed to the first channel back into the first volume of the measurement module or into a first volume of another measurement module.

21. The method of claim 20, wherein, the first volume comprises a solution characterized by a first osmolality;

the second volume comprises a second solution characterized by a second osmolality; and further comprising controlling the difference between the first osmolality and the second osmolality.

22. The method of claim 21, wherein controlling the difference between the first osmolality and the second osmolality comprises introducing an additional solution into the first volume to establish a desired difference in osmolality between the solution in the first volume and the solution in the second volume.

23. The method of claim 20, further comprising:

causing the re-introduced macromolecule to be translocated from the first volume into the second volume through the nanopore; and detecting a property correlated with the translocation of the re-introduced macromolecule through the nanopore.

24. A macromolecule sequencing apparatus comprising a plurality of the macromolecule sequencing devices of claim 1.

* * * * *